US005658415A

United States Patent [19]
Montemurro et al.

[11] Patent Number: 5,658,415
[45] Date of Patent: Aug. 19, 1997

[54] COMPOSITION AND PROCESS FOR ATTACHING ARTIFICIAL NAILS

[76] Inventors: Elizabeth Montemurro; Andrew J. Montemurro, both of 12 Underwood St., Patchogue, N.Y. 11772

[21] Appl. No.: 321,682

[22] Filed: Oct. 12, 1994

[51] Int. Cl.⁶ ........................ C09J 4/04
[52] U.S. Cl. ............ 156/331.2; 132/73; 156/61; 206/581; 523/105; 525/295; 526/298
[58] Field of Search ............ 156/57, 61, 331.2; 523/105; 526/298; 525/295; 132/73; 206/581

[56] References Cited

U.S. PATENT DOCUMENTS

| | | | |
|---|---|---|---|
| 4,038,345 | 7/1977 | O'Sullivan et al. | 525/295 |
| 4,105,715 | 8/1978 | Gleave | 526/298 |
| 4,106,614 | 8/1978 | Aylott | 132/73 |
| 4,440,910 | 4/1984 | O'Connor | 525/295 |
| 4,450,848 | 5/1984 | Ferrigno | 132/73 |
| 4,615,348 | 10/1986 | Nakata et al. | 132/73 |

FOREIGN PATENT DOCUMENTS 326288  8/1989  European Pat. Off. ........ 132/73

*Primary Examiner*—John J. Gallagher
*Attorney, Agent, or Firm*—St. Onge Steward Johnston & Reens LLC

[57] ABSTRACT

A process and a composite adhesive composition for applying artificial nails eliminate the need for fabrics or the application of initiators, solvents or catalysts as part of the nail application process. A preferred form of the composition comprises: cyanoacrylate adhesive and a powdered, polymeric filler in a stable, clear suspension, preferably having a viscosity of from about 100 to about 1000 cP as measured by a Brookfield viscometer at 25° C. using a No. 1 spindle at 20 rpm, formed for example from two cyanoacrylates, one having a viscosity of less than about 100 cP and the other having a viscosity of at least 1000 cP. The powdered, polymeric filler enhances the strength of the cured cyanoacrylate and preferably comprises poly (ethyl methacrylate).

11 Claims, No Drawings

COMPOSITION AND PROCESS FOR ATTACHING ARTIFICIAL NAILS

TECHNICAL FIELD

The invention relates to compositions for attaching artificial nails, particularly artificial finger nails, and to the processes made possible due to the provision of the new compositions. More specifically, the invention provides compositions and processes which greatly simplify the application of artificial nails and shorten the time required for application.

The application of artificial finger and toe nails has several benefits—some for purely cosmetic purposes and some for therapeutic or prosthetic reasons. For purposes of beauty, many individuals take great care to assure that their nails are in perfect condition. However, due to the time involved in attaching and manicuring artificial nails according to conventional procedures, many people simply cannot find the time to satisfy their personal desires for impeccable appearance. For therapeutic purposes, such as strengthening weak or shortened nails to permit them to grow, the currently available procedures also suffer from the time involved. For both purposes, the currently available techniques suffer from relatively easy damage by water.

There is a present need for new compositions and procedures for rapidly, simply, and securely attaching attractive artificial nails which have the ability to withstand long periods of contact with water.

BACKGROUND ART

Over the years, the art has provided a wide variety of structures, compositions and procedures for applying artificial nails. The known methods provide wholly preformed attachments, in situ nail formation, and combinations of preforms with in situ techniques.

In U.S. Pat. No. 4,222,399, M. Ionescu describes an artificial nail which is built up on a flat, flexible resilient form which is mounted on the natural nail to be improved. According to the procedure, a layer of a mush of resin powder and a liquid solvent is deposited on the form while on the natural nail, the form is then removed from the nail and the solvent is evaporated. The resulting artificial nail is then attached to the natural nail with an adhesive and filed into conformity with the natural nail. While this procedure is presented as an alternative to the formation of the artificial nail directly and completely on the natural nail, it can easily be seen that this procedure is also very time consuming and requires a high degree of skill.

In U.S. Pat. No. 4,384,058, G. Galante provides a nail lacquer composition comprising a film-forming agent, a compatible solvent, and an auxiliary resin to increase the wear resistance of the composition when dry. The auxiliary resin can be an alkyl cyanoacrylate, a styrene-acrylonitrile-acrylic terpolymer, or a mixture of these. The disclosure does not, however, provide any guidance on the attachment of artificial nails.

In U.S. Pat. No. 4,450,848, E. L. Ferrigno discloses an artificial nail forming composition, kit and method. According to the method, a conventional artificial fingernail is first glued onto a natural nail, leaving a space between the rear end of the artificial nail and the cuticle. A thin coating of a liquid cyanoacrylate adhesive is applied to the top surface of the natural finger nail in the space between the cuticle and the artificial nail. Next, a thin layer of an acrylic ester powder is adhered and a second thin coating of the adhesive is applied. After the composite of three layers dries, it is buffed until smooth. The disclosure indicates the provision of two separate adhesive components in addition the separate package of powder. This procedure, accordingly, is time consuming and tends to be wasteful.

In U.S. Pat. No. 4,552,160, G. D. Griggs provides a method for attaching an artificial nail using an ethyl alpha cyanoacrylate and a rayon fiber material applied over a conventional artificial nail applied with adhesive. The method requires the surface of the artificial nail and the natural nail to be buffed until they are substantially flush. Then the rayon is applied thereover and saturated with the cyanoacrylate. Following drying, the top surface is buffed. Again, this procedure is quite complicated and time consuming.

In U.S. Pat. No. 4,615,348, C. Natakata and T. Takenaka describe a method for adhering an artificial nail to a natural one by the use of an adhesive containing at least one specific α-cyanoacrylate for the purpose of reducing the generation of heat and easy removal of the adhesion. The adhesives were subjected to a series of tests, but no improvement in the standard procedures for attaching nails but achieving a continuous top nail surface was offered.

In U.S. Pat. No. 4,626,428, R. Weisberg and L. J. Krebaum describe a process for applying a protective acrylic coating to nails which is said to require a minimum of skills. The disclosed process, however, includes six steps the key feature of which seems to be the application of first a layer of a slow-curing cyanoacrylate glue, then a powdered polymethylacrylate, and an overcoat of a blend of acrylate monomers which must be cured. This procedure, because it employs at least three applications of separate materials, is not as simple as would be desired.

In U.S. Pat. No. 4,646,765, D. E. Cooper and D. A. Cooper describe the attachment of a composite of a cyanoacrylate compound and graphite fibers to a natural nail as either a nail extender or coating. The procedure calls for spraying an accelerator onto the nail following application of the above compound. The use of carbon fibers and the cyanoacrylate mix to extend nails requires the use of a template properly positioned and carefully removed at the right time. The added complication of spraying the accelerator takes time and creates the possibility of inconsistent results.

In U.S. Pat. No. 4,844,102, W. G. Repensek and R. Blomquist describe a procedure which entails the application of an artificial nail in three steps. First, a conventional artificial nail tip is cemented to the natural nail with the aid of a suitable, but not critical, adhesive which can be a cyanoacrylate or other adhesive. Then, the whole surface (including the top of both the artificial and exposed natural nail surface) is coated with a viscous cyanoacrylate adhesive. After application of the viscous mixture, it is necessary to apply a solvent mixture to spread it smoothly. Also, the solvent contains a polymerization initiator to speed the curing process. It would be desirable to have a procedure and composition which did not require such specialized components and steps.

In U.S. Pat. No. 5,319,011, Schoon discloses that cyanoacrylate resins can be cured more rapidly by contacting them with an organotin compound. In the context of artificial nail attachment, the nails are formed in situ by covering a nail surface with a layer of fabric and then applying a layer of a cyanoacrylate adhesive. After the surface has become stabilized, the organotin compound is then applied, such as by brushing or spraying. It would be desirable to provide a procedure which did not require the use of fabric or the subsequent application of an organotin or other composition which adds to the complexity and time involved.

In view of the state of the art which is represented not only by the above patents, but by countless other procedures and compositions, there remains a present need for a composition and process for rapidly and simply securing an artificial nail to a natural one and then finishing the surface to provide a natural-appearing and attractive nail.

DISCLOSURE OF INVENTION

It is an object of the invention to provide a composition for rapidly and simply securing an artificial nail to a natural one and then finishing the surface to provide a natural-appearing and attractive nail.

It is another object of the invention to provide a process for rapidly and simply securing an artificial nail to a natural one and then finishing the surface to provide a natural-appearing and attractive nail.

It is yet another and more specific object of the invention to provide a process, composition and kit for applying an artificial nail which eliminate the need for fabrics or the application of initiators, solvents or catalysts to the surface of the nail to complete the application process.

It is a still further object of the invention to provide a process for preparing a new composition for applying artificial nails which eliminates the need for fabrics or the application of initiators, solvents or catalysts.

It is a further object of the invention to greatly facilitate the application of artificial nails and achieve results which have improved resistance to water.

The invention provides a new composition, a new process and a new kit which meet these objectives. The invention also provides a process for preparing the composition of the invention.

The nail-securing composition comprises: a composite adhesive composition comprising a cyanoacrylate adhesive and a powdered, polymeric filler in a stable, clear suspension.

Preferably, the composite adhesive comprises cyanoacrylate adhesive having a viscosity of from about 100 to about 1000 cP. This viscosity and all of those stated in this disclosure, are as measured by a Brookfield viscometer at 25° C. using a No. 1 spindle at 20 rpm. Most preferably, the cyanoacrylate component is a blend of two cyanoacrylate adhesives, one having a viscosity of less than about 100 cP (preferably from about 1 to about 25 cP) and the other having a viscosity of at least 1000 cP (preferably from about 1200 to about 2500 cP).

The powdered, polymeric filler is a strenthening component and preferably comprises an acrylic polymer, e.g., a member selected from the group consisting of poly (methyl methacrylate), poly (ethyl methacrylate), poly (methyl acrylate), copolymers formed with any suitable alkyl acrylate, alkyl methacrylate, acrylonitrile, or like monomer. Preferred average particle sizes fall within the range of from about 10 to about 100 microns, weight average.

The process according to the invention for applying an artificial nail to a natural human nail, comprises: cleaning the surface of the natural nail; applying a drop of adhesive to the back surface of an artificial nail tip; pressing the artificial nail tip onto the surface of the natural nail, leaving an exposed area of the natural nail uncovered by the artificial nail tip; applying to the surface of the artificial nail tip and the exposed surface of the natural nail, a clear suspension of a composite adhesive composition as described above; and, smoothing the adhesive composition over the surfaces to which it is applied to obtain a smooth appearance.

The process for preparing the preferred nail-securing, composite adhesive composition, comprises: (a) adding from about 20 to about 90% by weight of a first ethyl cyanoacrylate adhesive having a viscosity of less than about 100 cP and from about 10 to about 80% by weight of a second cyanoacrylate adhesive having a viscosity of at least 1000 cP to a mixing vessel having a cylindrical side wall and two circular end walls, a central axis extending between the centers of the circular end walls; (b) sealing the mixing vessel; (c) orienting the mixing vessel with the central axis in a substantially horizontal position; (d) rotating the mixing vessel about the central axis for a period of time sufficient to achieve a uniform, stable blend of the first and second cyanoacrylate; (e) opening the mixing vessel and adding at least a portion of a total of from about 2 to about 15% by weight of a powdered polymeric filler; (f) sealing the mixing vessel; (g) orienting the mixing vessel with the central axis in a substantially horizontal position; (h) rotating the mixing vessel about the central axis for a period of time sufficient to achieve a uniform, stable suspension of filler in the blend of cyanoacrylate; and (i) repeating steps (e) through (h) as necessary to complete the addition of the polymeric filler.

The kit of the invention for applying artificial nails preferably comprises: a nail-securing composition as described; plastic artificial nail tips; an applicator; and a nail file.

DETAILED DESCRIPTION OF THE PREFERRED EMBODIMENT

The following description sets out a preferred form of the invention which relates to new compositions and procedures for attaching artificial nails, particularly artificial finger nails, which greatly simplify the application of artificial nails and shorten the time required for application. The invention is presented in terms of a process, composition and kit for applying artificial nails which eliminate the need for fabrics or the application of initiators, solvents or catalysts to the surface of the nail to complete the application process.

The nail-securing adhesive composition is unique in its composition and in the manner in which it is prepared. It is, in fact, a composite adhesive and is liquid enough to be employed for the purpose of attaching artificial nail tips to natural nails and yet is suitably viscous when applied to function well as a top coat. Also, and importantly, the adhesive is a composite of a liquid cyanoacrylate and a polymeric filler which, while not detracting form the crystal-clear appearance of the liquid, acts as a reinforcing agent in the cured adhesive and eliminates the need for fabrics or fibers.

Conventional procedures often apply silk or other fabrics as a nail overcoating. This is very time consuming and skill intensive, and is eliminated by the invention without eliminating the structural integrity of the overcoating layer. The dried adhesive of the invention also tends to be more resistant to moisture than those of the prior art.

The nail-securing, composite adhesive composition comprises an adhesive component based on cyanoacrylate adhesive. These adhesives are well known generally and in the specific field of artificial nails as indicated in the above-cited patents. However, the invention combines a suitable cyanoacrylate adhesive with a powdered, polymeric filler to form a stable, clear suspension which is not only easily applied, but results in an internally-strengthened coating.

Preferably, the composite adhesive comprises cyanoacrylate having a viscosity of from about 100 to about 1000 cP (centipoise). As noted above, this viscosity and all of those stated in this disclosure, are as measured by a Brookfield viscometer at 25° C. using a No. 1 spindle at 20 rpm. As commercially available, the cyanoacrylates are in the form of liquid monomer or a mixture of liquid monomers. These commercial compositions often contain thixotropic agents, both organic and inorganic, and polymerization inhibitors, such as hydroquinone, to extend shelf life. These materials can equally be employed in the composition of the present invention. It is emphasized again, however, that the polymeric filler of the invention is not simply a viscosity increasing agent and is, in fact, not employed for this purpose.

The cyanoacrylates as a group are preferred because of their quick setting and their strong adhesion to natural nails as well as most of the typical artificial nail materials. The alkyl cyanoacrylates such as methyl cyanoacrylate, ethyl cyanoacrylate, propyl cyanoacrylate, and butyl cyanoacrylate, can be employed singly or in combination as the cyanoacrylate adhesive component—it being necessary only to match the adhesive properties to the desired substrates and polymeric fillers employed for strengthening. The ethyl cyanoacrylates are the materials of choice.

Preferably, the composite adhesive comprises cyanoacrylate having a viscosity of from about 100 to about 1000 cP (centipoise). Most preferably, the cyanoacrylate component is a blend of two cyanoacrylate adhesives, one having a viscosity of less than about 100 cP (preferably from about 1 to about 25 cP) and the other having a viscosity of at least 1000 cP (preferably from about 1200 to about 2500 cP), to achieve an acceptable viscosity for the intended purposes. The preferred viscosity range for the mixture of cyanoacrylates will be from about 150 to about 400 cP.

The powdered, polymeric filler is a strenthening component. It will be any material of any particle size that permits incorporation into the cyanoacrylate monomer liquid or mixture of liquid monomers without significantly opacifying the liquid or unduly increasing its viscosity, but yet is capable of increasing the film strength of the cured cyanoacrylate. The powdered polymeric filler is mixed with the cyanoacrylate liquid monomer to achieve a liquid which is of suitable viscosity to form a uniform coating when applied by a simple brush applicator, but yet will exert added strength due to the polymeric filler. While the filler has some effect on the viscosity of the adhesive, its primary function is to strengthen the film formed when the cyanoacrylate polymer is fully cured. This strengthening effect is achieved while still permitting a crystal-clear adhesive liquid.

Preferably, this strengthening filler comprises an acrylate polyester, e.g., a member selected from the group consisting of poly (methyl methacrylate), poly (ethyl methacrylate), poly (methyl acrylate), copolymers formed with any suitable alkyl acrylate, alkyl methacrylate, acrylonitrile, or like monomer. Typical of the suitable acrylate polyesters and copolymers are those prepared from monomers selected from the group consisting of methy acrylate, ethyl acrylate, propyl acrylate, butyl acrylate, methyl methacrylate, ethyl methacylate, propyl methacrylate, butyl methacrylate, acrylonitrile, and mixtures of at least two of these.

While unpigmented polymers are preferred, the invention is not limited to such and pigments such as titanium dioxide can be employed if desired for particular applications. The particle size is preferably small enough to permit ease of processing and not unduely cause visible specs in the finished liquid or coating prepared from it. Particle sizes within the range of from about 10 to about 100 microns will be effective, with preferred average particle sizes being from about 25 to about 75 microns, weight average. The powder can include processing aids, such as anticaking ingredients (e.g., silica) as needed and to the extent that they do not affect the functionality of the composite adhesive or final cured film prepared from it. Also, agents such as benzoyl peroxide can be coated on the surface of the polymer particles to better integrate these structural materials into the cured matrix, typically at a level of from about 0.1 to about 2% by weight.

The nail-securing adhesive composition can be packaged in a suitable bottle or other container and sold as is or as part of a kit containing a combination of items necessary for the task of attaching and finishing artificial nails. A preferred form of kit for applying artificial nails comprises a nail-securing composition as described, a set of plastic artificial nail tips (e.g., of a suitable material such as acrylic ester, nylon, cellulose acetate, or the like), an applicator, typically on the bottle containing the composition, and a nail file. If desired, a composition which softens any ridge formed at the end of the artificial nail tip can be employed to facilitate filing it smoothly into conformity with the natural nail. Also, if desired, a promoter or activator liquid as known to the art can be employed as known in the art to hasten the final curing of the cyanoacrylate.

The following example describes the preparation and use of a nail-securing adhesive composition of the type described above. The example is presented for the purpose of further illustrating and explaining the invention, and is not to be taken as limiting in any regard. Unless otherwise indicated, all parts and percentages are based on the weight of the components at the indicated stage of processing.

EXAMPLE

This example describes one specific process for preparing a nail-securing, composite adhesive composition according to the invention. The composition is prepared from the following components:

| Component | Parts |
| --- | --- |
| Ethyl cyanoacrylate, 5 cp[1] | 1200 |
| Ethyl cyanozcrylate, 1500 cp[2] | 800 |
| Poly (methyl methacrylaate/ ethyl methacrylate) powder[3] | 141 |

The first-listed ethyl cyanoacrylate is added first and the second-listed cyanoacrylate is then added to an upright, cylindrical mixing vessel. The vessel has a cylindrical side wall and two circular end walls, with a central axis extending between the centers of the circular end walls. After filling, the vessel is closed and nitrogen gas is flushed through suitable valves to assure removal of air prior to sealing for mixing. After closing the valves to seal the mixing vessel, the mixing vessel is positioned on a pair of rollers with the central axis in a substantially horizontal position. The mixing vessel is then rotated about the central axis for a period of time, e.g., about 1 hour, sufficient to achieve a uniform, stable blend of the first and second cyanoacrylate. Following mixing, the mixing vessel is rested in closed condition for about 1 day and then opened for the addition of about 25 parts of the powdered poly (methyl methacrylate) strengthening filler. The vessel is reclosed, flushed and rotated for from about 5 to about 10 minutes.

This latter sequence is repeated as necessary to complete the addition of the polymeric filler and to achieve a uniform, stable suspension of filler in the blend of cyanoacrylate wherein the filler has become clear and not apparently visible.

The above composition is then filled into ½ ounce, drug oval high density polyethylene bottles with brush top applicators. The composition is then used to apply an artificial nail to a natural human nail. The nail is prepared by cleaning the surface of the natural nail with nail polish remover. A drop of the adhesive composition is applied to the back surface of an artificial nail tip. The nail tip is then pressed onto the surface of the natural nail, leaving an exposed area of the natural nail uncovered by the artificial nail tip. A ridge at the back of the tip, adjacent to the exposed area of the natural nail is typically formed and is filed to eliminate an unsightly line. The adhesive composition, which is a clear suspension, is applied to the surface of the artificial nail tip and the exposed surface of the natural nail with smoothing to obtain a smooth appearance. The nail is then filed and coated with nail polish in the same manner as would be done with a natural nail.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims. For conciseness, several conventions have been employed with regard to listings of chemicals and ranges. The listings of chemical entities throughout this description are meant to be representative and are not intended to exclude equivalent materials, precursors or active species. Also, each of the ranges is intended to include, specifically, each integer, in the case of numerical ranges, and each species, in the case of chemical formulae, which is encompassed within the range. The claims are meant to cover the claimed components and steps in any sequence which is effective to meet the objectives there intended, unless the context specifically indicates the contrary.

The invention claimed is:

1. A process for applying an artificial nail to a natural human nail, comprising: cleaning the surface of the natural nail; applying a drop of an adhesive composition comprising a blend of a first cyanoacrylate adhesive having a viscosity of less than about 100 cP and a second cyanoacrylate adhesive having a viscosity of at least 1000 cP, the resulting blend having a viscosity of from about 100 to about 1000 cP, and containing a powdered, polymeric filler to the back surface of an artificial nail tip; pressing the artificial nail tip onto the surface of the natural nail, leaving an exposed area of the natural nail uncovered by the artificial nail tip; applying to the surface of the artificial nail tip and the exposed surface of the natural nail, a clear suspension of the same adhesive composition; and smoothing the same adhesive composition over the surfaces to which it is applied as a top coat to obtain a smooth appearance.

2. A process according to claim 1 wherein the powdered, polymeric filler comprises an acrylic polymer or copolymer.

3. A process according to claim 2 wherein the powdered, polymeric filler has an average particle size of from about 10 to about 100 microns, weight average.

4. A process according to claim 1 wherein the adhesive comprises a blend of from about 20 to about 90% of first ethyl cyanoacrylate adhesive having a viscosity of less than about 100 cP and from about 10 to about 80% of a second ethyl cyanoacrylate adhesive having a viscosity of at least 1000 cP, the resulting blend being a cyanoacrylate adhesive having a viscosity of from about 100 to about 1000 cP as measured by a Brookfield viscometer at 25° C. using a No. 1 spindle at 20 rpm; and wherein the powdered, polymeric filler is employed at a level of from about 2 to about 15% by weight based on the weight of the adhesive composition, and comprises an acrylate polyester or copolymer prepared from a monomer selected from the group consisting of methy acrylate, ethyl acrylate, propyl acrylate, butyl acrylate, methyl methacrylate, ethyl methacylate, propyl methacrylate, butyl methacrylate, acrylonitrile, and mixtures of at least two of these, having an average particle size of from about 10 to about 100 microns, weight average.

5. A nail-securing composition comprising:

a composite adhesive composition comprising a cyanoacrylate adhesive containing a blend of two adhesives, from about 20 to about 90% by weight of one having a viscosity of less than about 100 cP and from about 10 to about 80% by weight of a second having a viscosity of at least 1000 cP and from about 2 to about 15% by weight of a strengthening powdered, polymeric filler, wherein the powdered, polymeric filler comprises an acrylate polymer or copolymer prepared from a monomer selected from the group consisting of methy acrylate, ethyl acrylate, propyl acrylate, butyl acrylate, methyl methacrylate, ethyl methacylate, propyl methacrylate, butyl methacrylate, acrylonitrile, and mixtures of at least two of these and having an average particle size of from about to 10 to about 100 microns, weight average, in a stable, clear suspension formulated to function as an nail adhesive and a top coat.

6. A process for preparing a composite nail-securing adhesive composition according to claim 5 comprising:

(a) adding from about 20 to about 90% of first ethyl cyanoacrylate adhesive having a viscosity of less than about 100 cP and from about 10 to about 80% of a second cyanoacrylate adhesive having a viscosity of at least 1000 cP to a mixing vessel having a cylindrical side wall and two circular end walls, a central axis extending between the centers of the circular end walls;

(b) sealing the mixing vessel;

(c) orienting the mixing vessel with the central axis in a substantially horizontal position;

(d) rotating the mixing vessel about the central axis for a period of time sufficient to achieve a uniform, stable blend of the first and second cyanoacrylate;

(e) opening the mixing vessel and adding at least a portion of a total of from about 2 to about 15% of a powdered polymeric filler;

(f) sealing the mixing vessel;

(g) orienting the mixing vessel with the central axis in a substantially horizontal position;

(h) rotating the mixing vessel about the central axis for a period of time sufficient to achieve a uniform, stable suspension of filler in the blend of cyanoacrylate;

(i) repeating steps (e) through (h) as necessary to complete the addition of the polymeric filler.

7. A process according to claim 6 wherein the vessel is flushed of air following each opening.

8. A process according to claim 7 wherein the first cyanoacrylate, the second cyanoacrylate, and the powdered polymeric filler are added in the proportions of from about 60:40:7, based on weight.

9. A process according to claim 7 wherein the powdered, polymeric filler comprises an acrylate polyester or copolymer prepared from a monomer selected from the group consisting of methyl acrylate, ethyl acrylate, propyl acrylate, butyl acrylate, methyl methacrylate, ethyl methacylate, propyl methacrylate, butyl methacrylate, acrylonitrile, and mixtures of at least two of these, and has an average particle size of from about 10 to about 100 microns.

10. A kit for applying artificial nails, comprising:

a nail-securing composite adhesive composition and top coat comprising a blend of a first cyanoacrylate adhesive having a viscosity of less than about 100 cP and a second cyanoacrylate adhesive having a viscosity of at least 1000 cP, the resulting blend having a viscosity of from about 100 to about 1000 cP, and a strengthening powdered, polymeric filler in a stable, clear suspension;

plastic artificial nail tips;

an applicator; and a nail file.

11. A kit for applying artificial nails according to claim 10 wherein the powdered, polymeric filler comprises an acrylate polymer or copolymer prepared from a monomer selected from the group consisting of methyl acrylate, ethyl acrylate, propyl acrylate, butyl acrylate, methyl methacrylate, ethyl methacylate, propyl methacrylate, butyl methacrylate, acrylonitrile, and mixtures of at least two of these, and prior to blending has an average partical size of from about 10 to about 100 microns, weight average.

* * * * *